United States Patent
Ryu et al.

(10) Patent No.: US 12,146,222 B2
(45) Date of Patent: Nov. 19, 2024

(54) METAL COATING METHOD FOR PLASTIC OUTER SHAPE REQUIRING ROBUSTNESS

(71) Applicant: IMTECHNOLOGY.CO., LTD, Seongnam-si (KR)

(72) Inventors: Seung Kyun Ryu, Seoul (KR); Sook Eun Baek, Seoul (KR)

(73) Assignee: IMTECHNOLOGY.CO., LTD, Seongnam-si (KR)

( * ) Notice: Subject to any disclaimer, the term of this patent is extended or adjusted under 35 U.S.C. 154(b) by 0 days.

(21) Appl. No.: 17/421,162

(22) PCT Filed: Jan. 8, 2019

(86) PCT No.: PCT/KR2019/000287
§ 371 (c)(1),
(2) Date: Jul. 7, 2021

(87) PCT Pub. No.: WO2020/145424
PCT Pub. Date: Jul. 16, 2020

(65) Prior Publication Data
US 2022/0056588 A1  Feb. 24, 2022

(30) Foreign Application Priority Data

Jan. 8, 2019 (KR) .................. 10-2019-0002287

(51) Int. Cl.
*C23C 18/16* (2006.01)
*A61F 2/58* (2006.01)
(Continued)

(52) U.S. Cl.
CPC .......... *C23C 18/1641* (2013.01); *A61F 2/583* (2013.01); *C23C 18/1698* (2013.01); *C23C 18/2006* (2013.01); *C23C 18/32* (2013.01)

(58) Field of Classification Search
CPC ............ C23C 18/1641; C23C 18/1698; C23C 18/2006; C23C 18/32; C23C 18/1653;
(Continued)

(56) References Cited

U.S. PATENT DOCUMENTS

2007/0003753 A1* 1/2007 Asgari .................... A61L 27/28
623/926
2007/0059449 A1* 3/2007 Ryu ...................... C23C 18/285
427/535

(Continued)

FOREIGN PATENT DOCUMENTS

CN       108245305 A    7/2018
EP       1 258 229 A1   11/2002
(Continued)

OTHER PUBLICATIONS

International Search Report and Written Opinion mailed Oct. 7, 2019 in International Application No. PCT/KR2019/000287, in 10 pages. (English translation of ISR in 2 pages.).

*Primary Examiner* — Dah-Wei D. Yuan
*Assistant Examiner* — Nga Leung V Law
(74) *Attorney, Agent, or Firm* — Bridgeway IP Law Group, PLLC; Jihun Kim

(57) ABSTRACT

This application relates to a metal coating method for plastic outer part requiring robustness. In the metal coating method, first, provide a plastic outer part as a motion assistance tool. Thereafter, a cold plasma treatment is performed to introduce a polar functional group to a surface of the plastic outer part by treating the plastic outer part with cold plasma. Next, a metal coating layer is formed on the surface of the plastic outer part treated with the cold plasma by an electroless plating method. Thereafter, an adhesive strength improvement process of improving an adhesive strength between the metal coating layer and the plastic outer part to 1,000 g/cm²

(Continued)

or more by heat treatment of the plastic outer part with the metal coating layer thereon is performed.

6 Claims, 9 Drawing Sheets

(51) Int. Cl.
*C23C 18/20* (2006.01)
*C23C 18/32* (2006.01)

(58) Field of Classification Search
CPC ..... C23C 18/208; C23C 18/285; C23C 18/30; C23C 18/405; C23C 18/1662; C23C 18/1692; C23C 18/31; C23C 18/38; C23C 18/52; C23C 18/20; C23C 18/204; C23C 18/2046; C23C 18/2053; C23C 18/206; C23C 18/2066; C23C 18/2073; C23C 18/2086; C23C 18/28; A61F 2/583; A61F 2/5046; A61L 2420/04; A61L 27/306; A61L 2420/02; B33Y 80/00; B25J 9/0006; B25J 11/0075; B29K 2105/0017
See application file for complete search history.

(56) References Cited

U.S. PATENT DOCUMENTS

2008/0195170 A1* 8/2008 Asgari .................... A61L 27/56
607/36
2017/0073816 A1* 3/2017 Hyman ................. C23C 14/021

FOREIGN PATENT DOCUMENTS

| JP | S63-270455 A | | 11/1988 |
|---|---|---|---|
| KR | 10-2002-0071437 A | | 9/2002 |
| KR | 10-2018-0025959 A | | 3/2018 |
| KR | 20180025959 A | * | 3/2018 |
| WO | WO 2010/018358 A2 | | 2/2010 |
| WO | WO 2017/005985 A1 | | 1/2017 |

* cited by examiner

FIG. 1
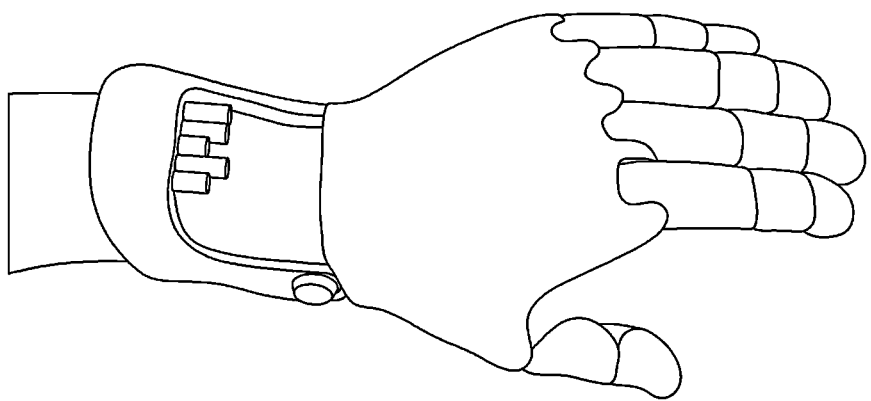
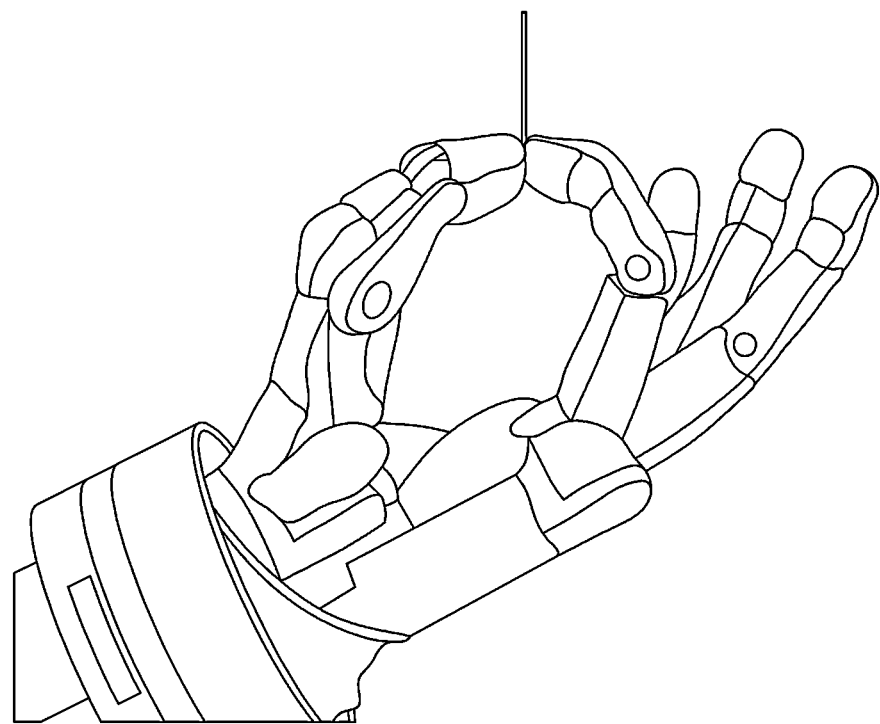

FIG. 2
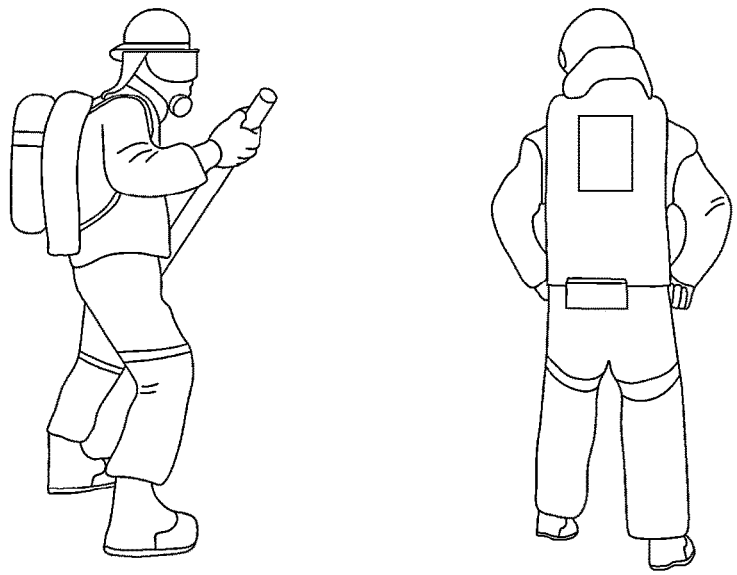
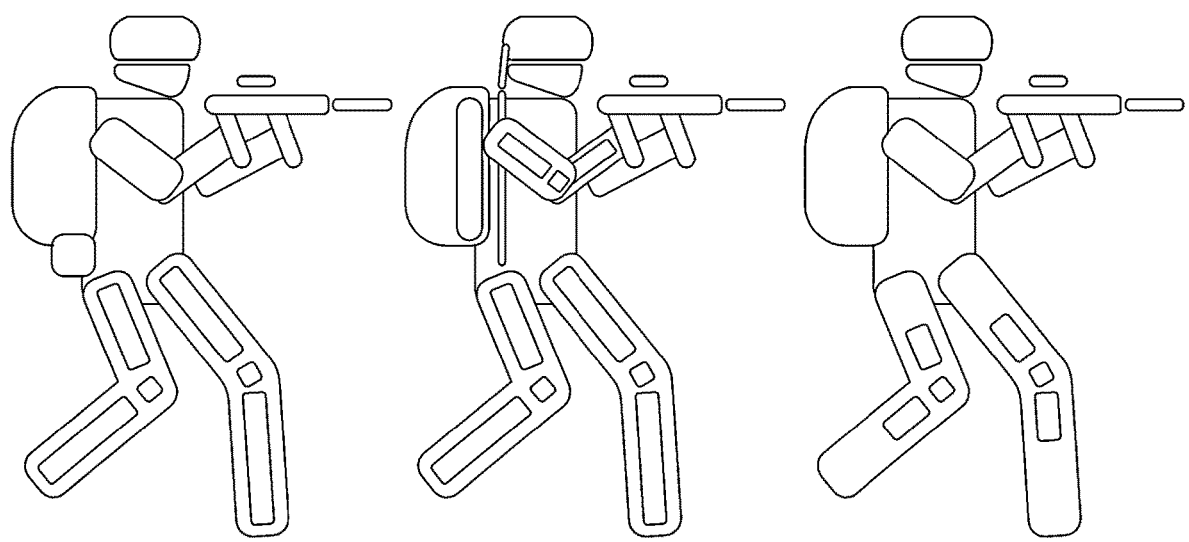

FIG. 4
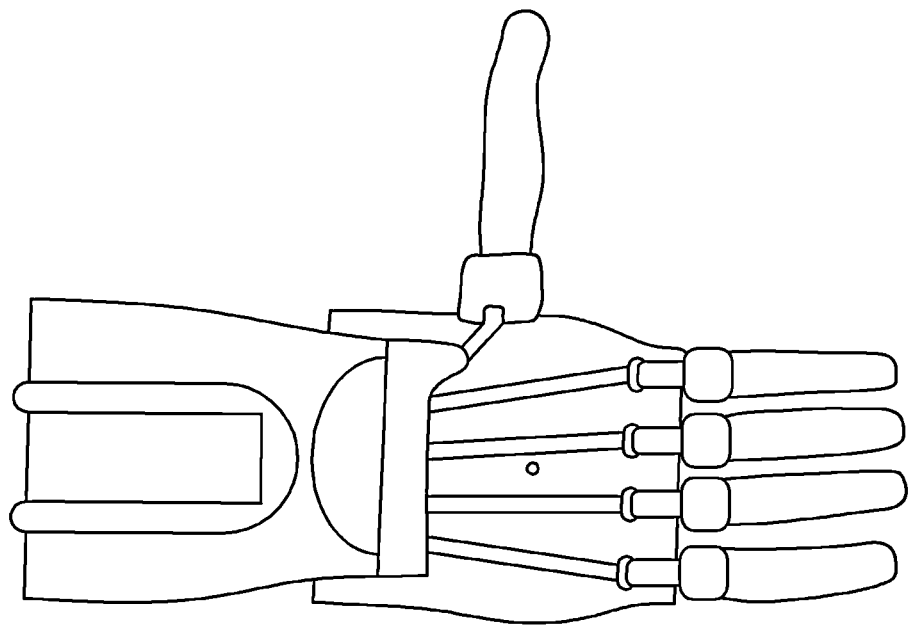
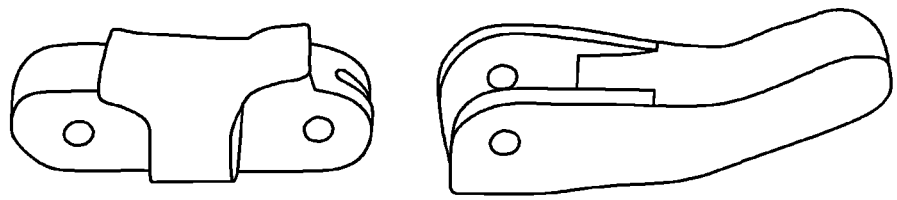

FIG. 5
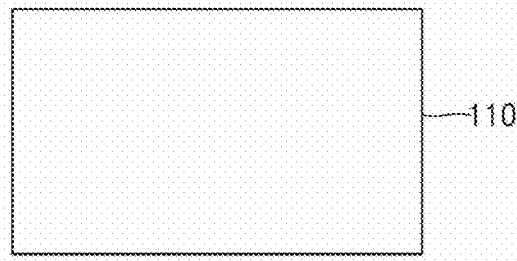
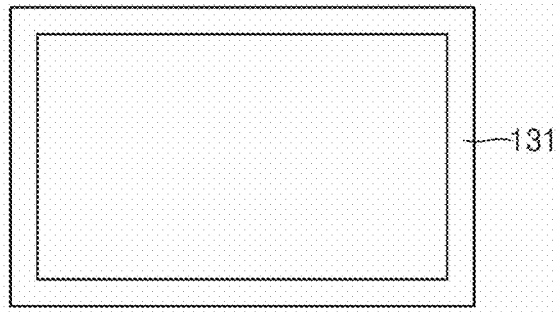
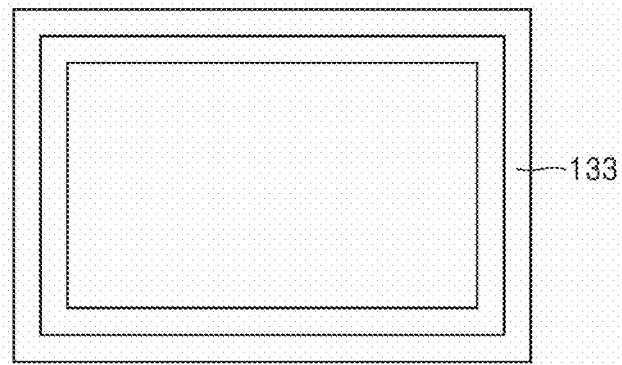

METAL COATING METHOD FOR PLASTIC OUTER SHAPE REQUIRING ROBUSTNESS

The present application is a U.S. national phase application under 35 U.S.C. § 371 of International Application No. PCT/KR2019/000287, filed on Jan. 8, 2019, which claims the benefit of Korean Patent Application No. 10-2019-0002287 filed on Jan. 8, 2019, in the Korean Intellectual Property Office, the entire disclosure of each of which is incorporated herein by reference.

TECHNICAL FIELD

The present disclosure relates to a metal coating method for plastic outer part requiring robustness, and more particularly, to a metal coating method for plastic outer part requiring robustness that may improve adhesive strength between a plastic outer part and a metal coating layer formed on a surface thereof.

BACKGROUND ART

A success or failure of healthy social activities of the congenital or acquired disabled is absolutely dependent on a rehabilitation assistance device that may restore a lost function. In particular, compared to before an accident, patients with upper extremity amputation have only lost hand functions, may move freely, and are fully aware of their existing expertise and their social roles, so they may continue to perform their role as a member of society like a normal person if they wear a hand prosthesis which is an assistance device replacing the function of the hand.

The hand prosthesis is largely classified into three types for each function. The first type is an aesthetic hand prosthesis with only the appearance of the hand without any function, and the second type is a semi-automatic hand prosthesis with a simple gripping function by motions of other body parts. The last type is a myoelectric hand prosthesis having a strong gripping force and capable of gripping various objects.

MYOBOCK hand (OttoBock Co) is a representative myoelectric hand prosthesis, and may implement gripping and rotating motions of the hand. However, in the case of the MYOBOCK hand, the weight of the hand prosthesis itself reaches 460 g, and a hand prosthesis system including a controller is expensive and heavy.

Recently, a lot of research on humanoid robot hands grafting robot technology to hand prosthesis has been conducted. To implement the finger bending motion, ACT Hand, UBH III Hand, and Anthropomorphic hand with 16 degrees of freedom used a simpler wire-motor mechanism than the existing gear-link-motor mechanism. However, the total weight of the hand including an actuator is more than 1 kg, which is heavy for patients with upper extremity amputation to wear for a long time.

Therefore, a finger model that may be applied to light and multiple degrees of freedom hand prosthesis and a finger model that may effectively use myoelectric hand prosthesis for disabled people with upper extremity amputation are being developed. However, research on durable materials for myoelectric hand prosthesis is still at a rudimentary level.

FIG. 1 is a view illustrating an example of a plastic hand prosthesis (top figure) and an aluminum hand prosthesis (bottom figure) as a wearable assistance tool.

In some examples, a high-strength aluminum material is used in the finger part of myoelectric hand prosthesis to overcome the limitation of low-strength plastic, and ribs are added to increase the bending rigidity of the finger. In addition, in order to increase the rigidity, a protective film treatment was performed by anodizing. However, in the case of amputation patients with extreme occupations using agricultural implements and lawn mowers, the fingers were bent when using myoelectric hand prosthesis for a long time.

3D printing technology is also being used in the development of medical devices such as the aforementioned hand prosthesis. The 3D printing technology has been mainly utilized in the field of prototyping because direct production from digital data is possible without a mold. In addition, due to limitations in surface roughness, mechanical strength, and rigidity, compared to an output of a general plastic injection process or cutting process, the 3D printing technology has been used more as a prototype for product visualization or assembly testing than for actual parts.

The 3D printing technology is very effective to be used for customized small-volume products because direct production from digital data is possible as mentioned above.

Exoskeleton, which has been recently developed a lot, refers to an exoskeleton robot that resembles a body skeleton. The use of the exoskeleton is largely classified into three categories: medical; military; and industrial. Among them, medical exoskeleton, which refers to exoskeleton mainly developed for paralyzed patients or people with weak physical functions, is worn on a disabled body and instantly senses an electrical signal according to the body's movement through a sensor and adds strength to the necessary parts. Through such a medical exoskeleton, a person with a physical disability may lift a heavy object very lightly, and a disabled person with a weak physical function may walk or move an arm to carry out daily life without difficulty.

FIG. 2 is a view illustrating an example of a wearable robot for firefighting (upper figure) and an exoskeleton robot for combat (bottom figure) as a wearable assistance tool.

Recently, South Korean small and medium-sized enterprise developed a wearable robot for firefighters and received attention from the media. However, a test result showed that a battery operated in less than 20 minutes in a high load environment similar to an actual use environment, such as firefighters wearing gear and climbing stairs in a high-rise building.

Therefore, for practical use, it is necessary to reduce the weight of the robot and increase the capacity of the battery. However, in order to solve this problem, there is a limitation in that the development of a suitable material must be prioritized. Therefore, the development of materials and manufacturing methods suitable for robots is required.

The exoskeleton of an exoskeleton structure has a potential to become a staple of all modern military of the world, so the United States of America, China, South Korea, Australia, Russia and the European Union are developing military exoskeleton. However, as research is still ongoing, no country has yet adopted an exoskeleton that may be worn over military uniforms.

The defense industry wants an exoskeleton that is lightweight and has long battery life, which is inexpensive and clearly offers advantages to soldiers. However, generals want a wearable exoskeleton that is not cumbersome to wear.

In order to have properties suitable for these requirements, the material should be light, strong, reliable, and easy to mold to be optimized for the individual soldier's body.

Therefore, there is a demand for the development of new materials that go beyond the limitations of existing materials.

DESCRIPTION OF EMBODIMENTS

Solution to Problem

A technical problem to be achieved by this disclosure is to provide a metal coating method for plastic outer part requiring robustness, with increased rigidity and increased adhesive strength between a plastic outer part and a metal coating layer formed on a surface.

The technical problem to be achieved by this disclosure is not limited to the above-mentioned technical problem, and other technical problems not mentioned are clearly to those with ordinary knowledge in the technical field to which this disclosure belongs from the description below may be understood.

Technical Solution to Problem

In order to achieve the above technical problem, an embodiment of the present disclosure provides a metal coating method for plastic outer part requiring robustness. In the metal coating method for plastic outer part requiring robustness, first, a plastic outer part is provided as a motion assistance tool. Thereafter, cold plasma treatment is performed to introduce a polar functional group to a surface of the plastic outer part by treating the plastic outer part with cold plasma. Next, a metal coating layer is formed on the surface of the plastic outer part treated with the cold plasma by an electroless plating method. Thereafter, an adhesive strength improvement process of improving an adhesive strength between the metal coating layer and the plastic outer part to 1,000 g/cm2 or more is performed by heat-treating the plastic outer part with the metal coating layer thereon.

In an embodiment of the present disclosure, in the increasing of adhesive strength, heat treatment may be performed by heating the plastic outer part with the metal coating layer thereon to a temperature below the softening point of the plastic outer part for 5 minutes to 200 minutes.

In an embodiment of the present disclosure, due to the increasing of adhesive strength, the adhesive strength between the metal coating layer and the plastic outer part may be increased by more than 10 times that in a wet pretreatment method of plating a metal after wet pretreatment of a plastic surface.

In an embodiment of the present disclosure, due to the increasing of adhesive strength, the adhesive strength between the metal coating layer and the plastic outer part may be increased to 10,000 g/cm2 or more.

In an embodiment of the present disclosure, in the forming of the metal coating layer, the metal coating layer is made of an alloy containing at least one of nickel, copper, and chromium, and due to the increasing of adhesive strength, a tensile strength to hardness (N/mm$^2$/Hv), defined as the tensile strength (N/mm$^2$) of the plastic outer part with the metal coating layer thereon with respect to the hardness (Hv) of the metal coating layer, is 3.00 N/mm$^2$/Hv or more.

In an embodiment of the present disclosure, in the forming of the metal coating layer, a thickness of the metal coating layer may be equal to or more than 5 μm, and due to the increasing of adhesive strength, a bending strength (Kg) of the plastic outer part with the metal coating layer thereon may be increased by 15% or more than the case in which the metal coating layer is not formed.

In an embodiment of the present disclosure, in the forming of the metal coating layer, at least a portion of the metal coating layer may contain organic and inorganic particles of Teflon (polytetrafluoroethylene, PTFE) or a boron (B) compound.

In an embodiment of the present disclosure, in the step of providing the plastic outer part as the motion assistance tool, the plastic outer part is produced through injection molding or 3D printing method, and a biodegradable plastic decomposed in nature may be used as the plastic.

Advantageous Effects of Disclosure

An embodiment of the present disclosure may provide a metal coating method for plastic outer part requiring robustness, with increased adhesive strength between a plastic outer part and a metal coating layer formed on a surface, with increased rigidity such as tensile strength and flexural strength, and with increased wear resistance.

The effect of the present disclosure is not limited to the above effect, and it should be understood to include all effects that may be inferred from the configuration of the disclosure described in the detailed description or claims of the present disclosure.

BRIEF DESCRIPTION OF DRAWINGS

FIG. 1 is a view illustrating an example of a plastic hand prosthesis and an aluminum hand prosthesis as a wearable assistance tool.

FIG. 2 is a view illustrating an example of a wearable robot for firefighting and an exoskeleton robot for combat as a wearable assistance tool.

FIG. 4 is a view illustrating a hand prosthesis as an example of a plastic outer part coated by the coating method for plastic outer part requiring robustness according to an embodiment of the present disclosure.

FIGS. 5 and 6 are views for explaining an example of the coating method for plastic outer part requiring robustness according to an embodiment of the present disclosure.

BEST MODE

Figure 3:
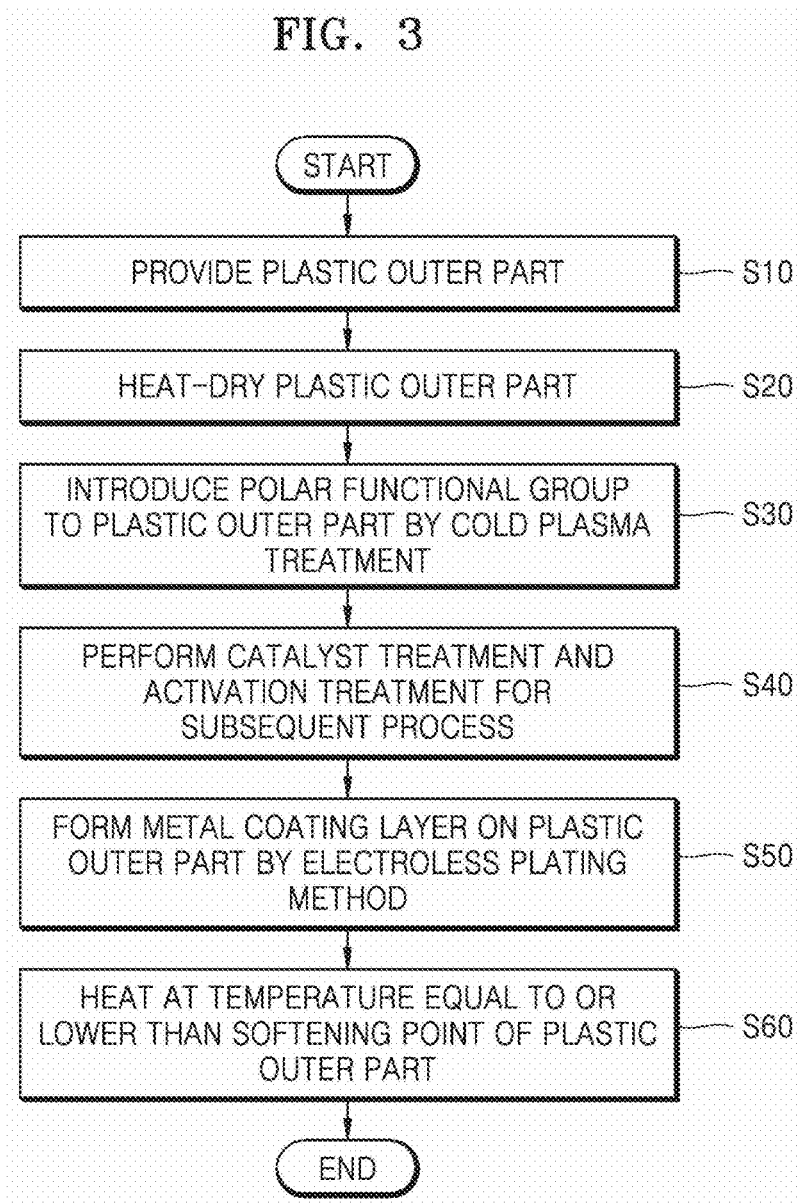
FIG. 3 is a flowchart for explaining a coating method for plastic outer part requiring robustness according to an embodiment of the present disclosure.

Hereinafter, the present disclosure will be described with reference to the accompanying drawings. However, the present disclosure may be implemented in several different forms, and thus is not limited to the embodiments described herein. And in order to clearly explain the present disclosure in the drawings, parts irrelevant to the description are omitted, and similar reference numerals are attached to similar parts throughout the specification.

Throughout the specification, when a part is "connected (connected, contacted, coupled)" with another part, it is not only "directly connected" but also "indirectly connected"

with another member in between. It includes the case of "connected to". Also, when a part includes a certain component, it means that other components may be further provided without excluding other components unless otherwise stated.

The terms used in this specification are only used to describe specific embodiments, and are not intended to limit the present disclosure. The singular expression includes the plural expression unless the context clearly dictates otherwise. In this specification, terms such as "comprise" or "have" are intended to designate that the features, numbers, steps, operations, components, parts, or combinations thereof described in the specification exist, and one or more other features It should be understood that this does not preclude the existence or addition of numbers, steps, operations, components, parts, or combinations thereof.

Hereinafter, an embodiment of the present disclosure will be described in detail with reference to the accompanying drawings.

FIG. 3 is a flowchart for explaining a coating method for plastic outer part requiring robustness according to an embodiment of the present disclosure. FIG. 4 is a view illustrating a hand prosthesis as an example of a plastic outer part coated by the coating method for plastic outer part requiring robustness according to an embodiment of the present disclosure.

Recently, a production of hand prosthesis, which is a body assistance tool, using a 3D printer has become a hot topic. Using the 3D printer, it is economical and may make a hand prosthesis suitable for the disabled in a short time, so many developments for this are made. However, the hand prosthesis made by the 3D printing method using plastic as a material lacks strength and durability, so it is very useful for the recovery of lost body parts, but there are many problems in using it in real life. Accordingly, there is a growing need for the development of light and robust materials.

In a metal coating method for plastic outer part requiring robustness, first, a plastic outer part 110 (refer to FIGS. 5 and 6) is provided as a motion assistance tool (S10).

Next, a thermal drying process of thermal drying the plastic outer part 110 to remove a cleaning agent and moisture from the surface of the plastic outer part 110 may be performed (S20).

Thereafter, a polar functional group is introduced to enable plating of the surface of the plastic outer part 110 by treating the surface of the thermally dried plastic outer part 110 with cold plasma (S30).

Next, the surface of the plastic outer part 110 treated with the cold plasma may be catalyzed and activated for a subsequent process (S40).

Next, metal is plated on the surface of the plastic outer part 110 by an electroless plating method to form a metal coating layer 131 (refer to FIGS. 5 and 6) (S50).

After forming the metal coating layer 131, an adhesive strength improvement process for improving adhesive strength between the plastic outer part and the metal coating layer 131 by heating for 5 minutes to 200 minutes at a temperature below a softening point of the plastic outer part to remove gas, moisture, cleaning agent, etc. may be further performed (S60). Through this adhesive strength improvement process, the adhesive strength between the metal coating layer and the plastic outer part may be increased to 2,000 g/cm$^2$ or more, preferably 10,000 g/cm$^2$ or more.

Hereinafter, each process will be described in more detail with reference to FIGS. 3 to 7.

Figure 6:
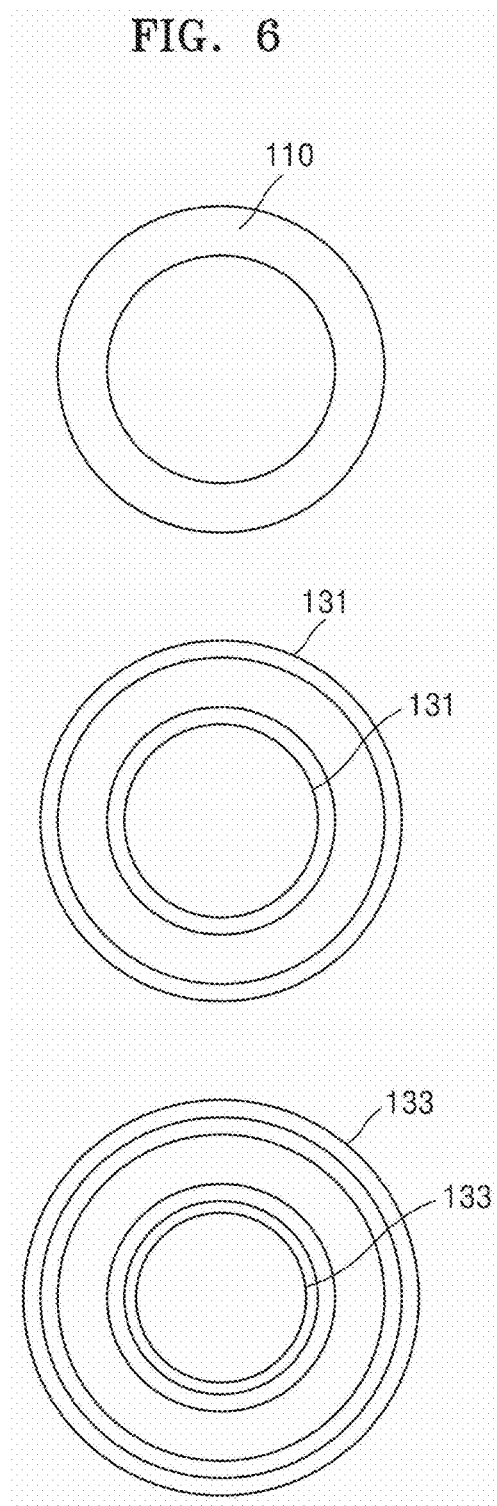

FIGS. 5 and 6 are views for explaining an example of the coating method for plastic outer part requiring robustness according to an embodiment of the present disclosure.

Figure 7:
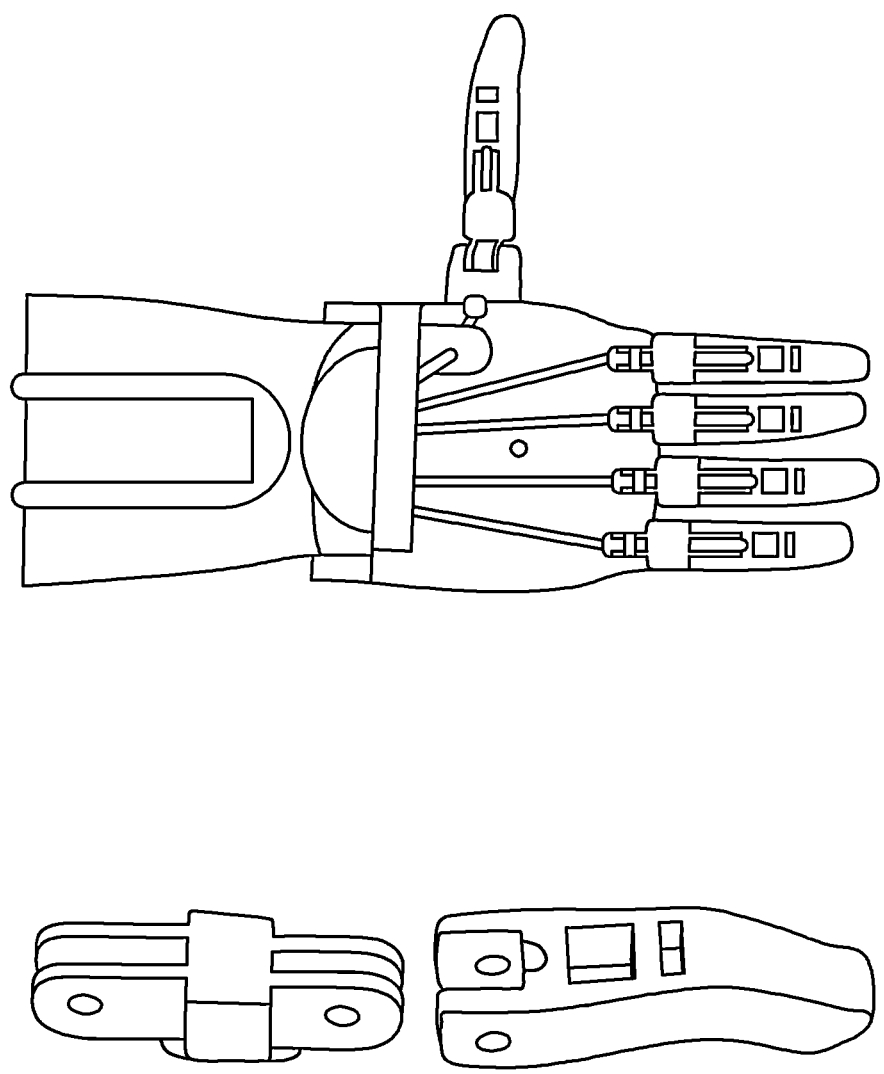
FIG. 7 is a view illustrating an example of a hand prosthesis coated with metal by the coating method for plastic outer part requiring robustness according to an embodiment of the present disclosure.

FIG. 7 is a view illustrating an example of a hand prosthesis coated with metal by the coating method for plastic outer part requiring robustness according to an embodiment of the present disclosure.

In the metal coating method for plastic outer part requiring robustness, first, the plastic outer part 110 is provided (S10). The plastic outer part 110 may have such a shape as a hand prosthesis, a leg prosthesis, an exoskeleton worn by a firefighter, an exoskeleton for battle worn by a soldier, as illustrated in FIGS. 1 and 2.

The plastic outer part 110 may be made of a polymer material including a resin or a polymer. The plastic outer part 110 may be formed by injection of resin or plastic, stamping into a mold, or 3D printing. For cost or ease of custom fabrication, the 3D printing method may be appropriate. As the plastic, biodegradable plastic that is decomposed in nature may be used. As the biodegradable plastic, for example, a plastic containing plant powder, poly ethic acid (PLA), poly caprolactone (PCL), etc. may be used.

The plastic outer part, such as the hand prosthesis, may include a joint mechanism such as a hinge and a support such as a finger or arm. These may be metal coated together by a process to be described later, or may be metal coated and then combined.

In the hand prosthesis, a part such as the joint part of the finger has a thin thickness and a lot of movement, which causes severe wear and has a great influence on the lifespan of the hand prosthesis. In order to reduce the friction of the joint part, a metal coating layer containing organic and inorganic particles of Teflon (polytetrafluoroethylene, PTFE) or boron (B) compound may be formed on at least a part of the hand prosthesis.

Next, inspection and cleaning may be carried out. For example, after inspecting an external defect of the plastic outer part 110, contaminants such as fingerprints, dust, and organic matter may be visually inspected, and ultrasonic cleaning may be performed using an ultrasonic cleaner.

Next, thermal drying may be performed (S20). For example, by removing the cleaning agent of the surface of the plastic outer part 110 by hot air in the oven, and removing the moisture absorbed in the cleaning process, it may be possible to prevent a decrease in process pressure in the post process due to moisture and gas.

After the thermal drying process, the surface of the plastic outer part 110 may be continuously treated with cold plasma to introduce the polar functional group (S30). For example, after putting the plastic outer part 110 in a vacuum chamber, a hydrophilic functional group is introduced into the surface of the plastic outer part 110 by the cold plasma to change into a plated structure.

Through the cold plasma treatment process, a contact angle of the surface of the plastic outer part 110 with respect to H$_2$O may be greatly reduced, and the contact angle may be maintained between 10° to 50°, and thus an effect of a subsequent metal plating process may be increased.

Even if a polymer material is treated with an ion beam such as hydrogen in a reactive gas such as oxygen, a polar functional group may be generated on the surface, but in this case, the treatment cost is high because it must be operated under a high vacuum. Therefore, in particular, using the cold plasma operated under a low vacuum near 10 Torr, it is possible to generate a polar functional group on the surface at a much lower cost.

When substances, such as acetone or acetic acid, that may embody a polar group on the surface due to the presence of oxygen is activated with plasma and reacted with a polymer material such as polyethylene (PE) or polypropylene (PP), a polar functional group such as C=O or O—H may be formed on the surface. The generation of the polar functional group may be immediately confirmed by measuring the contact angle with respect to $H_2O$ on the surface of the treated plastic outer part 110 or by irradiating a hydroxyl group or a carbonyl group with an infrared absorption spectrometer. In addition, by controlling treatment time and operating conditions of a plasma generator, a degree of generation of a functional group may be adjusted appropriately for the type of metal to be plated or the required film thickness.

Polymer material, commonly referred to as plastic, is a material with strong hydrophobicity, although there are differences depending on constituent elements of monomer. Polyether ether ketone (PEEK), polyphenylene sulfide (PPS), polycarbonate, fluorinated resin (Teflon, polytetrafluoroethylene, PTFE), and epoxy resin, which are often used as mechanical parts, have hydrophobicity.

Since the polymer material has insulating properties and is very stable, it is not easily oxidized and reduced, so a metal thin film may not be formed on the surface of the plastic outer part 110 by general electroless plating method, which is an electroplating or chemical reduction method. However, if there are many functional groups capable of accumulating metal ions on the surface of the polymer material, the metal thin film may be manufactured by the electroless plating method using a reducing agent.

For example, in the plasma treatment process for surface treatment of the plastic outer part 110 to form a metal coating layer 131 to be described later on the surface of the plastic outer part 110, using the cold plasma, the temperature of the plastic outer part 110 to be treated is below a glass transition point (Tg), and preferably the temperature in the vacuum chamber is below 50° C., in this state, the plasma treatment is performed.

In addition, it is preferable to generate plasma with one or a mixture of two or more selected from a group consisting of low concentration air, acetone, water, acetaldehyde, formalin, acrylic acid, oxygen, nitrogen, argon and hydrogen.

In the application of the electroless plating method after the cold plasma treatment according to this embodiment, the plastic outer part 110 to be applied may use polyether ether ketone (PEEK), poly phenylene sulfide (PPS), fluoro resin (polytetrafluoroethylene, PTFE), polyimide (PI), epoxy resin, and mixtures between these materials and organic or inorganic materials such as carbon fiber, glass fiber, and alumina, and the noble metal catalyst used is preferably palladium.

As mentioned above, in the plating method in this embodiment, using the method of cold plasma or ion implantation containing reactive gas, the hydrophilic functional group is generated on the surface of the plastic outer part 110, and the noble metal catalyst metal is adsorbed on the surface of the polar plastic outer part 110, and, in a state in which the metal ions to be plated are concentrated, the metal film is prepared by depositing the metal with a reducing agent without flowing electricity.

Next, after the cold plasma treatment, the catalyst treatment and the activation treatment may be performed (S40). For example, the plasma treated plastic outer part 110 is immersed in a mixture of 0.1 g/l to 100 g/l of catalyst (e.g., palladium chloride (PdCl2)) and 0.1 g/l to 100 g/l of stannous chloride (SnCl2) for 5 minutes. Thereafter, the activation treatment may be performed. For example, the catalytically treated plastic outer part 110 is subjected to activation treatment in a 50% to 60% hydrochloric acid solution at a temperature of 15° C. to 50° C. for 3 minutes and then washed three times.

In the electroless plating method, although heating is performed to activate the reducing agent, the polymer material is difficult to heat, so the catalyst may be used as described above. Palladium ions are easily reduced to a metallic state by the reducing agent, and have the advantage of providing activated hydrogen necessary for the reduction of thin film forming materials such as copper. Tin (Sn) added so that the palladium ions are well exposed is removed by washing with a weak acid solution (the hydrochloric acid solution described above).

More preferably, the hydrophilic functional group is introduced to the surface of the plastic outer part 110 by the cold plasma treatment, the plastic outer part 110 is immersed in the catalyst, and washed with hydrochloric acid. After that, a process of cleaning the plastic outer part 110 with the cleaning agent or the ultrasonic cleaner may be further included. By adding this process, the hydrophilic functional group introduced to the surface of the plastic outer part 110 may be ordered, and thus an effect of metal film plating in a subsequent process may be further increased.

Subsequently, the metal coating layer 131 may be formed by the electroless plating method (S50).

For example, in the case of copper plating, the plating is performed by immersing the activation-treated plastic outer part 110 into an electroless copper plating solution in which copper sulfate, formalin, caustic soda, ethylene diamine tetra acetic acid (EDTA), sodium bicarbonate, etc. are mixed for 60 minutes, and the metal coating layer 131 made of copper may be formed on the surface of the plastic outer part 110 by washing with water 3 times.

Alternatively, it is also possible to perform an electroless plating after immersing the plastic outer part 110 for 1 minute to 15 minutes at a temperature of 15° C. to 40° C. in an aqueous solution containing 20 ml/l to 150 ml/l sulfuric acid or hydrochloric acid.

The metal coating layer 131 to be plated may be a copper film, a nickel film, a chromium film, a noble metal film such as gold and silver, an alloy film of these metals, or a composite material film.

The metal coating layer 131 may have superior electromagnetic wave shielding properties than that of a light metal such as aluminum.

In this embodiment, after the process of plating the metal coating layer 131, the process of improving the adhesive strength may be performed (S60).

For example, a process of heating for 5 minutes to 200 minutes at a temperature below the softening point of the polymer material, which is the material of the plastic outer part 110, may be further performed. By this process, adhesive strength between the plastic outer part 110 and the metal coating layer 131 may be increased.

Medical instruments such as hand prosthesis, leg prosthesis, etc., wearable robot, exoskeleton robot, etc. having the plastic outer part 110 coated with the metal coating layer 131 according to this embodiment have increased mechanical performance and reduced mass. That is, high rigidity and strength are provided with respect to a weight ratio. Therefore, with respect to the weight ratio, it is very strong against external impact. In addition, as described above, the electromagnetic wave shielding ability may be significantly increased.

On the other hand, since the physical properties of the material are greatly affected by the type and physical properties of the metal to be plated on the outermost side, it is possible to form a metal having different physical properties or an alloy or a metal composite containing a metal depending on the purpose. That is, only the metal coating layer 131 may be used with only necessary functions, or secondary plating or tertiary plating may be performed according to the need for additional functions. In the subsequent plating processes such as the secondary plating and the tertiary plating, a metal layer suitable for the purpose of use may be plated on the outermost surface of the plastic outer part 110 by using a wet electroplating solution.

For example, in addition to the above-described metal coating layer 131, as an outermost surface layer 133, a high-density and high-corrosion resistant metal such as nickel or chromium is plated, or an outer surface layer may be formed with a metal plating solution of a specially formulated color.

In the case of the metal-coated plastic outer part obtained by this process, the metal coating layer 131 may be formed to have a thickness of about 5 microns or more, and the metal coating layer may be formed to have a dense structure.

In addition, through a test, results of increasing the strength by the metal coating layer 131 as shown in Table 1 below were obtained.

TABLE 1

Tensile strength test results of metal-coated plastic outer part

| Hardness (Hv) | Tensile strength (N/mm2) | Remark |
|---|---|---|
| 500 | 1,700 | Specific gravity of |
| 600 | 2,150 | alloy: Ni-P |
| 700 | 2,500 | 7.9Ni-B 8.6Cr alloy |
| 800 | 2,900 | 7.5 |
| 900 | 3,300 | |

For comparison, the tensile strength test results of 3D printing ABS material (ABS specific gravity: 1.05) are shown in Table 2 below.

TABLE 2

Tensile strength test results of 3D printing ABS material

| | Tensile strength | |
|---|---|---|
| Thickness | Maximum point stress (N/mm2) | Breaking point stress (N/mm2) |
| 2 mm | 24.0175 | 23.0561 |
| 3 mm | 30.2571 | 29.0415 |
| 4 mm | 29.6829 | 25.9814 |
| 5 mm | 27.1333 | 26.7841 |

In this embodiment, in the metal coating layer forming process, the metal coating layer may be made of an alloy containing at least one of nickel, copper, and chromium.

Referring to Tables 1 and 2, it may be seen that the strength of the metal-coated plastic outer part is significantly increased by coating a low-strength plastic with a high-strength metal alloy. In addition, it may be seen that the strength is further increased when the hardness of the metal alloy to be coated is increased.

When defining tensile strength to hardness (N/mm$^2$/Hv) as tensile strength (N/mm$^2$) of the plastic outer part with the metal coating layer thereon with respect to the hardness (Hv) of the metal coating layer, and when the tensile strength is divided by the hardness in Table 1, it may be seen that the tensile strength to hardness is approximately 3.40, 3.58, 3.57, 3.63, and 3.67, respectively.

According to the metal coating method for plastic outer part requiring robustness according to the present embodiment, even when the type of the plastic and the metal coating layer are different, the tensile strength to hardness may be estimated to be 3.0 or higher, which is similar to the above-described tensile strength to hardness. Such, the tensile strength to hardness is a result that may not be achieved by other plating methods, for example, the wet plating method described above, showing a remarkable effect of the method according to the present embodiment.

TABLE 3

Increase in strength by plating (poly phenylene sulfide (PPS))

| Plating thickness (μm) | Bending strength (Kg) | Strength increase (%) |
|---|---|---|
| 0 | 8.0 | 0 |
| 4 | 9.3 | 16 |
| 8 | 9.5 | 19 |

Referring to Table 3, the strength was increased by coating the metal film on the plastic, and the increase in strength was proportional to the plating thickness. In an embodiment of the present disclosure, in the forming of the metal coating layer, the thickness of the metal coating layer is formed to be 5 μm or more, and the bending strength (Kg) of the plastic outer part with the metal coating layer thereon due to the increasing of adhesive strength was increased by 15% or more than the case in which the metal coating layer is not formed. Therefore, referring to Tables 1, 2, and 3, it may be seen that it is effective to thickly coat a metal having a high hardness in order to obtain high strength.

Figure 8:
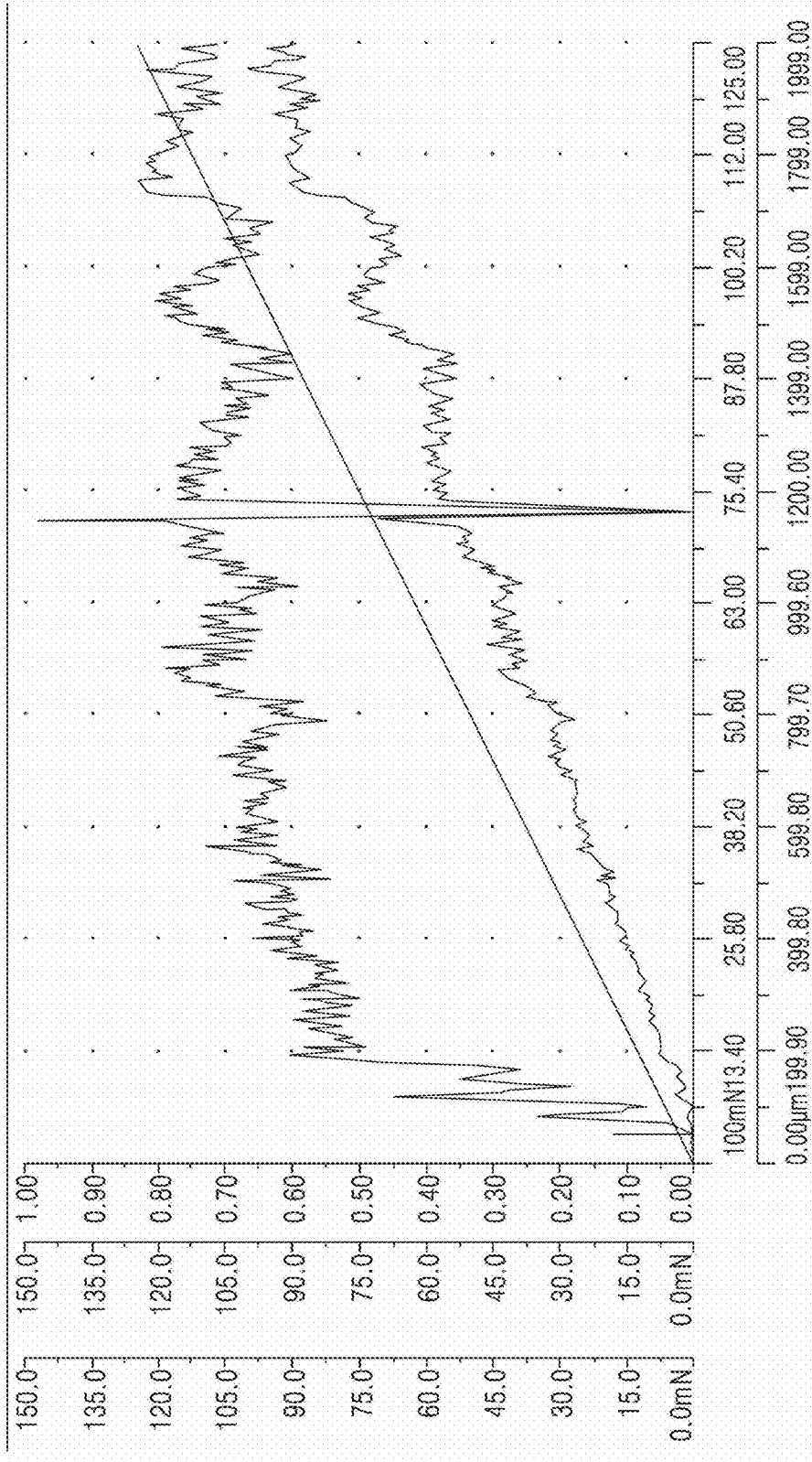
FIG. 8 is a graph illustrating a measurement result of a plating adhesive strength.
Figure 9:
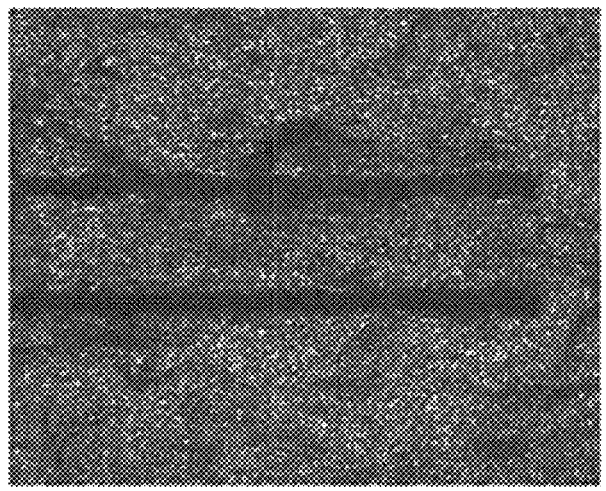
FIG. 9 is a view illustrating a measurement result of plating adhesive strength using a scratch tester.

FIG. 8 is a graph illustrating a measurement result of a plating adhesive strength. FIG. 9 is a view illustrating a measurement result of plating adhesive strength using a scratch tester.

To measure the adhesion of the plated metal film (the metal coating layer) to the plastic outer part, the adhesion was compared using ABS plastic specimen and a specimen made by a general chromic acid wet etching method (lower graph in FIG. 8) and the metal coating method for plastic outer part requiring robustness according to the present embodiment described above (upper graph in FIG. 8).

Referring to FIG. 8, the specimen prepared by the method according to the present embodiment had very high adhesive strength, so it was impossible to measure it using a conventional tensile tester. Therefore, the adhesive strength of the copper plating film was measured using a scratch tester.

TABLE 4

Comparison of plating adhesive strength

| | Wet pretreatment | Dry pretreatment |
|---|---|---|
| Adhesive strength (g/cm2) | 1,150 | 12,240 |

Referring to Table 4, the most commonly used method for plating metal on plastic is a wet pretreatment method using a mixture of chromic acid and sulfuric acid in an etching process. However, in the case of the wet pretreatment method, adhesive strength increases with etching time, but has a disadvantage that it may be applied only to plastics containing ABS. In addition, the adhesive strength is prescribed to be used at 1,000 g/cm² or more based on the automobile industry. In the product made by the plating method after dry pretreatment according to the metal coating method for plastic outer part requiring robustness according to this embodiment, the adhesive strength was 12,240 g/cm², which is more than 10 times that of the product made by the wet pretreatment method.

That is, in this embodiment, due to the above-described increasing of adhesive strength, the adhesive strength between the metal coating layer and the plastic outer part may be increased to 10,000 g/cm² or more, by more than 10 times compared to the wet pretreatment method of plating metal after wet pretreatment of the plastic surface. Therefore, it may be seen that the method of this embodiment is very reliable and has a remarkable effect.

TABLE 5

Comparison of properties of materials

|  | Plastic | Composite | Aluminum | Titanium | Steel | Present Embodiment |
|---|---|---|---|---|---|---|
| Weight (specific gravity) | 5(1.1) | 5(1.8) | 3(2.7) | 2(4.7) | 1(7.8) | 5(1.9) |
| 3D printing | 5 | 1 | 2 | 4 | 3 | 5 |
| Strength | 1 | 4 | 3 | 4 | 5 | 4 |
| Wear resistance | 1 | 2 | 2 | 3 | 4 | 5 |
| Processability | 4 | 3 | 4 | 1 | 2 | 5 |
| Price | 5 | 2 | 4 | 1 | 2 | 4 |
| Total | 16 | 12 | 15 | 13 | 16 | 23 |
| Rank | 2 | 6 | 4 | 5 | 3 | 1 |

Various materials are used for prosthetics and exoskeleton. And, the prosthesis and exoskeleton must be worn on the human body, have a structure similar to that of the human body, and have a large number of joint structures. In addition, a lot of force is concentrated on the prosthesis and the exoskeleton. Referring to Table 5, materials with high strength generally have a disadvantage in that they are heavy due to high density. On the other hand, plastic is light in weight and has excellent processability, but has the disadvantage of low strength and durability.

Materials such as lightweight and high-strength composite materials and titanium are expensive and have limitations in their use. The price of a functional electric hand prosthesis is expensive, about 40,000 dollars to 45,000 dollars, so there are many restrictions on the use of it by the general public or children of growing age.

Referring to Table 5, it may be seen that the material properties of products such as hand prosthesis manufactured according to this embodiment have the most excellent properties overall compared to other comparison objects.

According to this embodiment, by coating a conductive high-strength metal according to the method of the present disclosure after molding a hand prosthesis, leg prosthesis, industrial and military exoskeleton plastic outer part with plastic, it is possible to manufacture products with good processability, light weight, metal strength, electromagnetic wave shielding ability, and unique colors.

That is, by applying the injection molding process and the metal plating process, it is possible to significantly reduce the manufacturing costs compared to the case using the existing aluminum products, as well as greatly improve the characteristics such as weight reduction and strength increase in hand prosthesis, etc.

The description of the present disclosure described above is for illustration, and those of ordinary skill in the art to which this disclosure belongs can easily transform it into other specific forms without changing the technical spirit or essential characteristics of the present disclosure. you will be able to understand. Therefore, it should be understood that the embodiments described above are illustrative in all respects and not restrictive. For example, each component described as a single type may be implemented in a distributed manner, and likewise components described as distributed may also be implemented in a combined form.

The scope of the present disclosure is indicated by the following claims, and all changes or modifications derived from the meaning and scope of the claims and their equivalent concepts should be construed as being included in the scope of this disclosure.

MODE OF DISCLOSURE

It has been described together in the best form for implementation of the disclosure.

The invention claimed is:

1. A metal coating method for a plastic outer part of a prosthesis requiring robustness, the metal coating method comprising:
    providing the plastic outer part of the prosthesis, the prosthesis having a joint part;
    performing a cold plasma treatment by treating the plastic outer part with cold plasma to introduce a polar functional group to a surface of the plastic outer part;
    forming a metal coating layer, by an electroless plating method, on the surface of the plastic outer part which has been treated with the cold plasma, the electroless plating including depositing the metal coating layer with a reducing agent without flowing electricity; and
    heat-treating the plastic outer part and the metal coating layer thereon to increase an adhesive strength between the metal coating layer and the plastic outer part to 1,000 g/cm² or more,
    wherein in the forming of the metal coating layer, the metal coating layer comprises an alloy containing chromium, such that a tensile strength to hardness (N/mm²/Hv), defined as the tensile strength (N/mm²) of the plastic outer part with the metal coating layer thereon with respect to a hardness (Hv) of the metal coating layer, is 3.00 N/mm²/Hv or more, and
    wherein the metal coating layer includes a portion formed on the joint part of the prosthesis, and the portion of the metal coating layer formed on the joint part contains organic and inorganic particles of polytetrafluoroethylene (PTFE) or a boron (B) compound to reduce friction of the joint part,
    wherein, in providing the plastic outer part of the prosthesis, a plastic containing plant powder or poly ethic acid (PLA) is used as the plastic outer part of the prosthesis.

2. The metal coating method of claim 1, wherein, in the increasing of the adhesive strength, a heat treatment is performed by heating the plastic outer part with the metal coating layer thereon, at a temperature equal to or lower than a softening point of the plastic outer part for 5 minutes to 200 minutes.

3. The metal coating method of claim 1, wherein, due to the increasing of adhesive strength, the adhesive strength between the metal coating layer and the plastic outer part is increased by 10 times or more than that in a wet pretreatment method in which a metal is plated after a wet pretreatment of a plastic surface.

4. The metal coating method of claim 2, wherein, due to the increasing of adhesive strength, the adhesive strength between the metal coating layer and the plastic outer part is increased to 10,000 g/cm² or more.

5. The metal coating method of claim 2, wherein, in the forming of the metal coating layer, a thickness of the metal coating layer is 5 μm or more, and
   wherein, due to the increasing of adhesive strength, a bending strength (Kg) of the plastic outer part with the metal coating layer thereon is increased by 15% or more than a case in which the metal coating layer is not formed.

6. The metal coating method of claim 1, wherein, in the providing the plastic outer part of the prosthesis, the plastic outer part is produced through injection molding or three-dimensional (3D) printing method.

* * * * *